# US012296038B2

United States Patent
Kitaoka et al.

(10) Patent No.: US 12,296,038 B2
(45) Date of Patent: May 13, 2025

(54) TOPICAL COMPOSITION CONTAINING ASCORBIC ACID AND/OR SALT THEREOF

(71) Applicant: ROHTO PHARMACEUTICAL CO., LTD., Osaka (JP)

(72) Inventors: Yu Kitaoka, Osaka (JP); Mariko Iwai, Osaka (JP); Sho Yamashina, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 17/279,296

(22) PCT Filed: Sep. 25, 2019

(86) PCT No.: PCT/JP2019/037537
§ 371 (c)(1),
(2) Date: Mar. 24, 2021

(87) PCT Pub. No.: WO2020/067132
PCT Pub. Date: Apr. 2, 2020

(65) Prior Publication Data
US 2022/0031597 A1    Feb. 3, 2022

(30) Foreign Application Priority Data

Sep. 25, 2018 (JP) .................. 2018-179018

(51) Int. Cl.
| *A61K 8/67* | (2006.01) |
| *A61K 8/34* | (2006.01) |
| *A61Q 19/00* | (2006.01) |

(52) U.S. Cl.
CPC .............. *A61K 8/676* (2013.01); *A61K 8/345* (2013.01); *A61K 8/678* (2013.01); *A61Q 19/00* (2013.01); *A61K 2800/10* (2013.01); *A61K 2800/52* (2013.01); *A61K 2800/5922* (2013.01)

(58) Field of Classification Search
CPC ......... A61Q 19/08; A61K 8/676; A61K 8/678
See application file for complete search history.

(56) References Cited

U.S. PATENT DOCUMENTS

| 4,983,382 A | 1/1991 | Wilmott et al. |
| 5,140,043 A | 8/1992 | Darr et al. |
| 6,299,889 B1 | 10/2001 | Cowton et al. |
| 2005/0154054 A1 | 7/2005 | Zielinski et al. |
| 2006/0029687 A1 | 2/2006 | Vivier et al. |
| 2015/0189872 A1* | 7/2015 | Gradtke ............... A01N 31/04 514/730 |
| 2021/0052481 A1* | 2/2021 | Kitaoka ............... A61K 47/186 |

FOREIGN PATENT DOCUMENTS

| CN | 111511366 A | 8/2020 |
| JP | 2002-348228 A | 12/2002 |
| JP | 2004507561 A | 3/2004 |
| JP | 2005-225865 A | 8/2005 |
| JP | 2010-180206 A | 8/2010 |
| JP | 2013-095691 A | 5/2013 |
| JP | 2014-227386 A | 12/2014 |
| KR | 20100061954 A * | 6/2010 |
| WO | 2000/78283 A1 | 12/2000 |
| WO | 2002/19972 A2 | 3/2002 |
| WO | 2005070380 A1 | 8/2005 |
| WO | 2019-131892 A1 | 7/2019 |
| WO | 2019-189742 A1 | 10/2019 |

OTHER PUBLICATIONS

International Search Report dated Nov. 5, 2019 of PCT/JP2019/037537, filed Sep. 25, 2019.
Budavari et al., "9632. Beta-Tocopherol; 9633. Gamma-Tocopherol; 9634. Delta-Tocopherol; 9635. Epsilon-Tocopherol; 9636. Sigma1-Tocopherol; 9637. Sigma2-Tocopherol; 9638. Eta-Tocopherol; . . . 10159. Vitamin E," The Merck Index, Title page, copyright page, pp. 1620-1621, 1712 (1996).
Subra, "Diethylene Glycol Monoethyl Ether," in Handbook of Pharmaceutical Excipients, Title page, copyright page, pp. 256-258 (Raymond C. Rowe et al ed., 7th ed., 2012).
NS Ladyzhynsky, "Propylene Glycol," in Handbook of Pharmaceutical Excipients, Title page, copyright page, pp. 672-674 (Raymond C. Rowe et al ed., 7th ed., 2012).
Office action for Chinese Patent Application No. 201980062314.5, issued Jun. 27, 2023, pp. 1-20 (English translation included).
Office action issued in corresponding Chinese Patent Application No. 201980062314.5, dated Feb. 6, 2024, pp. 1-10, including English translation.
Decision on Rejection in related Chinese Application No. 201980062314.5, dated Jul. 3, 2024, pp. 1-14 (including English translation).

* cited by examiner

Primary Examiner — Gina C Justice
(74) Attorney, Agent, or Firm — Eventide Law LLC

(57) ABSTRACT

Provided is a very stable topical composition. A topical composition is prepared that contains (A) from 1 to 40% by mass of at least one type selected from the group consisting of ascorbic acid and salts of ascorbic acid; (B) at least 20% by mass of a diol having three carbon atoms; (C) at least one type selected from the group consisting of tocopherol, salts of tocopherol, and derivatives of tocopherol; and (D) water, wherein the mass ratio of component (D) to component (A) is from 0.5 to 5.0 and the topical composition includes less than 20% by mass of glycol ether.

4 Claims, No Drawings

TOPICAL COMPOSITION CONTAINING ASCORBIC ACID AND/OR SALT THEREOF

TECHNICAL FIELD

The present invention relates to a topical composition containing ascorbic acid and/or a salt thereof.

BACKGROUND ART

Ascorbic acid is known to exhibit a number of effects, such as an anti-inflammatory effect, an acne improving effect, a whitening effect, an anti-aging effect, an antioxidant effect, a cell activating effect by promoting the synthesis of biological components such as collagen, and the effect of suppressing cell damage and DNA damage caused by exposure of epidermal keratinocytes to ultraviolet light. It is widely used as a topical preparation on skin in anticipation of these effects.

Because ascorbic acid is readily oxidized in the presence of water such as the water in aqueous solutions, the amount of water has to be reduced in a preparation. However, ascorbic acid cannot be solubilized sufficiently in a small amount of water.

Therefore, various methods for stabilizing ascorbic acid in aqueous topical preparations for the skin have been studied. (See Patent Document 1: WO 2002/019972 A1, Patent Document 2: WO 2000/078283 A1, Patent Document 3: JP 2002-348228 A1, and Patent Document 4: JP 2005-225865 A).

CITATION LIST

Patent Literature

Patent Document 1: WO 2002/019972 A1
Patent Document 2: WO 2000/078283 A1
Patent Document 3: JP 2002-348228 A
Patent Document 4: JP 2005-225865 A

SUMMARY OF INVENTION

Technical Problem

It is an object of the present invention to provide a stable topical composition containing ascorbic acid which has good stability.

Solution to Problem

The present invention provides a topical composition containing ascorbic acid and/or salts thereof, in which ascorbic acid and/or salts thereof can be present in various concentrations.

In a study conducted by the present inventors, it was found that ascorbic acid and/or salts thereof sometimes decompose in storage even when blended at predetermined concentrations.

As a result of extensive research conducted to solve this problem, the present inventors discovered that topical compositions in which ascorbic acid or salts thereof are very stable could be obtained by compounding (A) from 1 to 40% by mass of at least one type selected from the group consisting of ascorbic acid and salts of ascorbic acid, (B) at least 20% by mass of a diol having three carbon atoms, (C) at least one type selected from the group consisting of tocopherol, salts of tocopherol, and derivatives of tocopherol, and (D) water, and by setting the mass ratio of component (D) to component (A) mass ratio from 0.5 to 5.0 and the amount of glycol ether at less than 20% by mass. The present invention is a product of this discovery.

Specifically, the present invention provides the topical compositions listed below.

Item 1. A topical composition comprising:
(A) from 1 to 40% by mass of at least one type selected from the group consisting of ascorbic acid and salts of ascorbic acid;
(B) at least 20% by mass of a diol having three carbon atoms;
(C) at least one type selected from the group consisting of tocopherol, salts of tocopherol, and derivatives of tocopherol; and
(D) water,
wherein the mass ratio of component (D) to component (A) is from 0.5 to 5.0 and the topical composition includes less than 20% by mass of glycol ether.

Item 2. A topical composition according to item 1, further comprising a lower alcohol.

Item 3. A topical composition according to item 1 or 2, wherein component (B) includes 1,3-propanediol.

Item 4. A topical composition according to any one of items 1 to 3, comprising at least 40% by mass of component (B).

Item 5. A topical composition according to any one of items 1 to 4, comprising no more than 0.5% by mass of component (C).

The present invention also provides the method for imparting stability to a topical composition below.

Item 6. A method for imparting stability to a topical composition comprising (A) at least one type selected from the group consisting of ascorbic acid and salts of ascorbic acid by compounding (A) from 1 to 40% by mass of at least one type selected from the group consisting of ascorbic acid and salts of ascorbic acid, (B) at least 20% by mass of a diol having three carbon atoms, (C) at least one type selected from the group consisting of tocopherol, salts of tocopherol, and derivatives of tocopherol, and (D) water, and by setting the mass ratio of component (D) to component (A) mass ratio from 0.5 to 5.0 and the amount of glycol ether at less than 20% by mass.

Advantageous Effects of Invention

The present invention can provide a very stable topical composition.

DESCRIPTION OF EMBODIMENTS

In the present specification, the unit amount is "mass %" which has the same meaning as "g/100 g."

The present invention is a topical composition comprising:
(A) from 1 to 40% by mass of at least one type selected from the group consisting of ascorbic acid and salts of ascorbic acid;
(B) at least 20% by mass of a diol having three carbon atoms;
(C) at least one type selected from the group consisting of tocopherol, salts of tocopherol, and derivatives of tocopherol; and
(D) water,
wherein the mass ratio of component (D) to component (A) is from 0.5 to 5.0 and the topical composition includes less than 20% by mass of glycol ether.

A topical composition of the present invention is stable and safe over a wide concentration range of (A) at least one type selected from the group consisting of ascorbic acid and salts of ascorbic acid. It also has an excellent product feel during use and transdermal absorbability.

[(A) at Least One Type Selected from the Group Consisting of Ascorbic Acid and Salts of Ascorbic Acid]

The ascorbic acid used in the present invention can be commercially available ascorbic acid used as a component in topical preparations for the skin in the fields of pharmaceuticals, quasi-drugs, and cosmetics. This is usually referred to as L-ascorbic acid.

Ascorbic acid salts can also be used. Here, the ascorbic acid salts are pharmaceutically acceptable salts. There are no particular restrictions, and examples include both salts with an organic base (for example, salts with tertiary amines such as trimethylamine salts, triethylamine salts, monoethanolamine salts, triethanolamine salts and pyridine salts, as well as basic ammonium salts such as arginine), and salts with an inorganic base (for example, alkali metal salts such as ammonium salts, sodium salts and potassium salts, alkaline earth metal salts such as calcium salts and magnesium salts, and aluminum salts). Preferred ascorbic acid salts are sodium salts and potassium salts. Specific examples include sodium ascorbate, sodium ascorbyl monophosphate esters, sodium ascorbyl diphosphate esters, sodium ascorbyl triphosphate esters, and sodium ascorbyl disulfate esters.

In the present invention, ascorbic acid and salts thereof can be used alone or in combinations of two or more.

In a topical composition of the present invention, the total amount of component (A) relative to the total amount of topical composition is set based on the balance with other components. The total amount of component (A) relative to the total amount of topical composition is 1% by mass or more, preferably 2% by mass or more, and more preferably 3% by mass or more. Also, the total amount of component (A) relative to the total amount of topical composition is 40% by mass or less, preferably 30% by mass or less, and even more preferably 25% by mass or less. The total amount of component (A) relative to the total amount of topical composition is 1% by mass to 40% by mass, preferably 2% by mass to 30% by mass, and more preferably 3% by mass to 25% by mass.

[(B) Diols Having Three Carbon Atoms]

There are no particular restrictions on the diols having three carbon atoms that are used in the present invention as long as they are used as a component in topical preparations for the skin in the fields of pharmaceuticals, quasi-drugs, and cosmetics. These diols having three carbon atoms can be commercially available products. There are no particular restrictions on the on the diols having three carbon atoms. Examples include 1,3-propylene diol (CAS Number: 504-63-2; English name: 1,3-dihydroxypropane or trimethylene glycol) and propylene glycol (CAS Number: 57-55-6; English name: 1,2-dihydroxypropane, Japanese alternate name: 1,2-propanediol). These can be used alone or in any combination. From the standpoint of relieving skin irritation, improving product feel during use, and suppressing preparation discoloration, the combination of 1,3-propanediol and propylene glycol is preferred, and the inclusion of at least 1,3-propanediol as component (B) is more preferred.

There are no particular restrictions on the total amount of component (B) relative to the total amount of topical composition, but it can be 20% by mass or more, preferably 25% by mass or more, more preferably 30% by mass or more, even more preferably 35% by mass or more, and still more preferably 40% by mass or more. Also, the total amount of component (B) relative to the total amount of topical composition is preferably 90% by mass or less, more preferably 85% by mass or less, and even more preferably 80% by mass or less.

There are no particular restrictions on the total amount of component (B) relative to the total amount of topical composition, but it is preferably 20 to 90% by mass, more preferably 25 to 85% by mass, even more preferably 30 to 80% by mass, and still more preferably 40 to 80% by mass.

In a topical composition of the present invention, there are no particular restrictions on the ratio of component (B) to component (A). However, 1 to 300 parts by mass is preferable, 1 to 100 parts by mass is more preferable, and 1 to 30 parts by mass is even more preferable per 1 part by mass component (A).

[(C) at Least One Type Selected from the Group Consisting of Tocopherol, Salts of Tocopherol, and Derivatives of Tocopherol]

The at least one type selected from the group consisting of tocopherol, salts of tocopherol, and derivatives of tocopherol (Vitamin E) used in the present invention can be any compound commonly used as a component in topical preparations for the skin in the fields of pharmaceuticals, quasi-drugs, and cosmetics. These may be any of d-tocopherol, l-tocopherol, and dl-tocopherol, or have an α, β, γ, or δ structure. There are no particular restrictions on the (C) at least one type selected from the group consisting of tocopherol, salts of tocopherol, and derivatives of tocopherol. Examples include tocopherols such as d-α-tocopherol, d-β-tocopherol, d-γ-tocopherol and d-δ-tocopherol, l-α-tocopherol, l-β-tocopherol, l-γ-tocopherol and l-δ-tocopherol, as well as mixtures such as dl-α-tocopherol, dl-β-tocopherol, dl-γ-tocopherol and dl-δ-tocopherol. There are no particular restrictions on tocopherol derivatives, but tocopherol esters are preferred. In particular, the tocopherol derivative can be any type selected from the group consisting of tocopheryl acetate, tocopheryl nicotinate esters or salts thereof, tocopheryl succinate or salts thereof, tocopheryl linoleate esters, tocopheryl phosphate or salts thereof, tocopheryl linoleate (or oleate), and tocotrienol. Especially preferred are tocopherol or tocopheryl acetate, which which may be in the d-form, l-form or dl-form, or may have an α, β, γ or δ structure.

These can be natural materials or synthesized, and commercially available products can be used.

These types of vitamin E can also be used alone or in combinations of two or more.

These types of vitamin E can contribute to the higher stability of a topical composition of the present invention.

In a topical composition of the present invention, there are no particular restrictions on the total amount of component (C) relative to the total amount of topical composition. However, 0.00001% by mass or more is preferred and 0.0001% by mass or more is especially preferred. The total amount of component (C) is preferably 10% by mass or less, and more preferably 5% by mass or less, based on the total amount of the topical composition. Also, the amount of the component (C) is preferably 0.00001 to 10% by mass, and more preferably 0.0001 to 5% by mass, based on the total amount of the topical composition.

[(D) Water]

A topical composition of the present invention is a liquid composition containing water. There are no particular restrictions on the proportion of water. However, it is preferably 0.01 to 60% by mass, more preferably 0.01 to 50% by mass, even more preferably 0.1 to 40% by mass, and still more preferably 1 to 30% by mass relative to the topical composition.

In a topical composition of the present invention, the ratio of component (D) to component (A) is preferably 0.5 to 5.0 parts by mass and more preferably 0.5 to 4.0 parts by mass per 1 part by mass of the total amount of component (A).

[Glycol Ethers]

From the standpoint primarily of improving stability, the present invention either does not contain a glycol ether such as ethoxydiglycol, or if it does, contains less than 20% by mass. There are no particular restrictions on the glycol ether constituting less than 20% by mass of the topical composition as long as it is used as a component in topical preparations for the skin in the fields of pharmaceuticals, quasi-drugs, and cosmetics. Here, in addition to ethoxydiglycol, the glycol ether can be any glycol ether used as a component in topical preparations for the skin in the fields of pharmaceuticals, quasi-drugs, and cosmetics in which 10 g or more can be dissolved in 100 g of water. The following examples have a degree of polymerization of 2 or less. These include diethylene glycol monomethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether. Other examples include diethylene glycol monomethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether. Typical examples include diethylene glycol monomethyl ether, diethylene glycol monopropyl ether, ethylene glycol monobutyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether.

These glycol ethers can also be used alone or in combinations of two or more.

In a topical composition of the present invention, the total amount of glycol ether such as ethoxydiglycol is less than 20% by mass, preferably 15% by mass or less, and more preferably 10% by mass or less, based on the total amount of the external composition. The topical composition may also be glycol ether free. Also, the total amount of glycol ether such as ethoxydiglycol is preferably 0% by mass or more and less than 20% by mass, more preferably 0% by mass to 15% by mass, and even more preferably about 0% by mass to 10% by mass.

In a topical composition of the present invention, the ratio of the glycol ether component to component (A) is preferably 0 to 10 parts by mass, and more preferably 0 to 5 parts by mass, per 1 part by mass of the total amount of component (A). In some situations, it may be 0.001 to 20 parts by mass or 0.01 to 10 parts by mass.

A topical composition of the present invention contains (A), (B), (C), and (D). A topical composition with good stability can also be obtained by using the defined amount of glycol ether.

[(E) Lower Alcohols]

From the standpoint of improving product feel during use, stability, and skin absorption, a topical composition of the present invention may include (E) a lower alcohol in addition to a glycol ether such as ethoxydiglycol when also including components (A), (B), (C) and (D) as long as the effects of the present invention are not impaired. There are no particular restrictions on the lower alcohols that are used in the present invention as long as they are used as a component in topical preparations for the skin in the fields of pharmaceuticals, quasi-drugs, and cosmetics. In the present specification, "lower alcohol" refers to an alcohol having from 1 to 6 carbon atoms. Among these, use of an alcohol having from 1 to 3 carbon atoms is preferred. Examples include methanol, ethanol, n-propanol, and isopropanol.

If a topical composition of the present invention contains a lower alcohol, the total amount of component (E) relative to the total amount of the topical composition is preferably 0.1% by mass or more, and more preferably 0.5% by mass or more. The total amount of component (E) is preferably 25% by mass or less, and more preferably 20% by mass or less.

The total amount of component (E) is preferably 0.001 to 30% by mass, more preferably 0.1 to 25% by mass, even more preferably 0.5 to 20% by mass, and still more preferably 1 to 20% by mass.

In a topical composition of the present invention, the ratio of component (E) to component (A) is preferably 0.01 to 10 parts by mass per 1 part by mass of the total amount of component (A).

[Polyhydric Alcohols]

When a topical composition of the present invention contains components (A), (B), (C) and (D), it may also contain a polyhydric alcohol in addition to the defined amount or less of glycol ether such as ethoxydiglycol as long as the effects of the present invention are not impaired.

There are no particular restrictions on the polyhydric alcohols that are used in the present invention as long as they are used as a component in topical preparations for the skin in the fields of pharmaceuticals, quasi-drugs, and cosmetics. There are no particular restrictions on the use of these polyhydric alcohols, which may be added for moisturizing or as a solubilizer. Specific examples include glycerin, diglycerin, dipropylene glycol, 1,3-butylene glycol, and 3-methyl-1,3-butanediol. Use of 1,3-butylene glycol or dipropylene glycol is preferred.

If used, the total amount of polyhydric alcohol other than component (B) is preferably 0.001 to 60% by mass, more preferably 0.01 to 50% by mass, even more preferably 0.1 to 40% by mass, and still more preferably about 0.5 to 30% by mass.

[pH Adjusters with an Amine or Amino Group]

From the standpoint of improving product feel during use, stability, and skin absorption, when a topical composition of the present invention contains components (A), (B), (C) and (D), it may also contain a pH adjuster with an amine or amino group in addition to a glycol ether such as ethoxydiglycol as long as the effects of the present invention are not impaired. There are no particular restrictions on the pH adjusters with an amine or amino group that are used in the present invention as long as they are used as a component in topical preparations for the skin in the fields of pharmaceuticals, quasi-drugs, and cosmetics. There are no particular restrictions on the pH adjusters with an amine or amino group. Examples include aspartic acid, s-aminocaproic acid, glutamic acid, amino ethyl sulfonic acid, monoethanolamine, triethanolamine, diisopropanolamine, triisopropanolamine, lysine, and low molecular weight betaine. Among these examples, use of low molecular weight betaine is especially preferred.

In the present invention, a low molecular weight betaine refers to one that forms zwitterions in a molecule having a molecular weight of 200 or less. Specific examples include quaternary ammonium bases, quaternary phosphonium bases, and tertiary sulfonium bases. These exhibit almost no properties as surfactants.

Specific examples include trimethylglycine, triethylglycine, tripropylglycine, triisopropylglycine, trimethyl-β-alanine, and trimethyl-γ-aminobutyric acid. Trimethylglycine is preferred.

These low molecular weight betaines may also be substituted. Specific examples include N,N,N-trimethylalanine, N,N,N-triethylalanine, N,N,N-triisopropylalanine, N,N,N-trimethylmethylalanine, carnitine, and acetylcarnitine. Carnitine is preferred.

These can be synthesized, but commercially available products can also be used.

These low molecular weight betaines can be used alone or in combinations of two or more.

A pH adjuster with an amine or amino group such as a low molecular weight betaine can be used when a topical composition of the present invention requires good transdermal absorbability.

In a topical composition of the present invention, there are no particular restrictions on the total amount of pH adjuster with an amine or amino group relative to the total amount of topical composition. However, 0.01% by mass or more is preferred, and 0.05% by mass or more is especially preferred. Also, the total amount of pH adjuster with an amine or amino group relative to the total amount of topical composition is preferably 25% by mass or less, and more preferably 20% by mass or less. The total amount of pH adjuster with an amine or amino group relative to the total amount of topical composition is preferably from 0.01% by mass to 25% by mass, and more preferably from 0.05% by mass to 20% by mass.

In a topical composition of the present invention, there are no particular restrictions on the ratio of pH adjuster with an amine or an amino group to component (A). However, the total amount per part by mass component (A) is preferably 0.00001 to 20 parts by mass, more preferably 0.0001 to 20 parts by mass, even more preferably 0.001 to 10 parts by mass, still more preferably 0.0025 to 5 parts by mass, and most preferably 0.01 to 3 parts by mass.

[3-O-Ethylascorbic Acid]

When a topical composition of the present invention contains components (A), (B), (C) and (D), it may also contain 3-O-ethylascorbic acid in addition to the defined amount or less of glycol ether such as ethoxydiglycol as long as the effects of the present invention are not impaired. 3-O-Ethylascorbic acid can be synthesized by ethoxylation of the hydroxyl group at the 3-position in ascorbic acid. (For a well-known method, see JP H08-134055 A.) The 3-O-ethylascorbic acid used can also be a commercially available product. There are no particular restrictions on the commercially available product that is used. Examples include "VC Ethyl" from Nippon Fine Chemical Co., Ltd. and products from Junsei Chemical Co., Ltd.

3-O-Ethylascorbic acid contributes to the stability of topical compositions of the present invention.

3-O-Ethylascorbic acid can also be used as a salt. Here, salts of 3-O-ethylascorbic acid are pharmaceutically acceptable salts. There are no particular restrictions, and examples include salts with organic bases (for example, salts with tertiary amines such as trimethylamine salts, triethylamine salts, monoethanolamine salts, triethanolamine salts and pyridine salts, and basic ammonium salts such as arginine), and salts with inorganic bases (for example, alkali metal salts such as ammonium salts, sodium salts and potassium salts, alkaline earth metal salts such as calcium salts and magnesium salts, and aluminum salts). Preferred salts of 3-O-ethylascorbic acid are sodium salts and potassium salts.

In the present invention, 3-O-ethylascorbic acid and salts thereof can be used alone or in combinations of two or more.

In a topical composition of the present invention, the total amount of 3-O-ethylascorbic acid or salts thereof relative to the total amount of the topical composition is set based on the balance with other components. Relative to the total amount of topical composition, the amount is preferably 0.005% by mass or more, more preferably 0.01% by mass or more, even more preferably 0.02% by mass or more, still more preferably 0.05% by mass or more, and most preferably 0.1% by mass or more. Also, the total amount of 3-O-ethylascorbic acid or salts thereof relative to the total amount of the topical composition is preferably 10% by mass or less, more preferably 5% by mass or less, even more preferably 3% by mass or less, and still more preferably 2% by mass or less. The total amount of 3-O-ethylascorbic acid or salts thereof relative to the total amount of the topical composition is preferably from 0.005 to 10% by mass, more preferably from 0.01 to 5% by mass, even more preferably from 0.02 to 3% by mass, and still more preferably from 0.05 to 2% by mass.

As for the ratio of 3-O-ethylascorbic acid or salts thereof to component (A) in a topical composition of the present invention, the total amount of 3-O-ethylascorbic acid or salts thereof per 1 part by mass of the total amount of component (A) is preferably from 0.0001 to 100 parts by mass, more preferably from 0.001 to 100 parts by mass, even more preferably from 0.005 to 10 parts by mass, and still more preferably from 0.005 to 1 part by mass.

[Surfactants]

A topical composition of the present invention may contain a surfactant as long as it does not impair the effects of the present invention. If a surfactant is used, a surfactant with an HLB of 8 to 20, preferably 8 to 18, more preferably 9 to 16, and even more preferably 10 to 15 can be used. These surfactants can contribute to the stabilization of component (C). Examples include polyoxyethylene hardened castor oil 40, polyoxyethylene hardened castor oil 60, polyoxyethylene hardened castor oil 80, polyoxyethylene polyoxypropylene decyltetradecyl ether, polyoxyethylene (20)/polyoxypropylene (4) cetyl ether, PEG-8 glyceryl isostearate, polyoxyethylene sorbitan monolaurate (20 E.O.), polyoxyethylene sorbitan isostearate (20 E.O.), polyoxyethylene sorbitan stearate (20 E.O.), polyglyceryl-10 coconut oil fatty acid ester, polyglyceryl-3 coconut oil fatty acid ester, PEG-7 glyceryl coconut oil fatty acid ester, polyglyceryl-10 dioleate, polyglyceryl-10 diisostearate, PEG-40 glyceryl triisostearate, PEG-40 glyceryl isostearate, polyglyceryl trilaurate-10, hexaglyceryl tricaprylate, polyglyceryl laurate, polyglyceryl myristate, and polyoxyethylene lauryl ether. Preferred examples include polyoxyethylene/polyoxypropylene decyltetradecyl ether, polyoxyethylene hardened castor oil 40, polyoxyethylene hardened castor oil 60, polyoxyethylene hardened castor oil 80, polyoxyethylene sorbitan monolaurate (20 E.O.), polyoxyethylene sorbitan isostearate (20 E.O.), and polyglyceryl laurate.

In a topical composition of the present invention, the total amount of surfactant relative to the total amount of the topical composition is set based on the balance with other components. The total amount of surfactant relative to the total amount of topical composition is preferably from 0.01 to 10% by mass, more preferably from 0.05 to 5% by mass, and even more preferably from 0.1 to 3% by mass.

[Other Components]

When a topical composition of the present invention contains components (A), (B), (C) and (D), it may also contain any of the following components in addition to the defined amount or less of glycol ether such as ethoxydiglycol in order to enhance or supplement the various actions of ascorbic acid or adding other useful actions. These components include whitening components, anti-inflammatory components, antibacterial components, cell activating components, astringent components, antioxidant components, acne improving components, biological component synthesis promoting components for collagen etc., blood circulation promoting components, moisturizing components, and anti-aging components. These components can be used alone or in combinations of two or more. Use of one or more components among whitening components, anti-inflammatory components, antibacterial components, cell activating components, astringent components, antioxidant components, anti-aging components, and moisturizing components is preferred. Preferred combinations of components include combinations with a whitening component, combinations with a whitening component and an antioxidant component, combinations with an antioxidant, combinations with an anti-aging component, and combinations with a whitening component and an anti-aging component. There are no particular restrictions on these components as long as they are currently used as components in topical preparations for the skin in the fields of pharmaceuticals, quasi-drugs, and cosmetics, and will be used in the future.

In addition to the components mentioned above, a topical composition of the present invention may also contain solubilizing components, oils and fats, sugars, and transdermal absorption promoting components. In particular, the use of solubilizing components or oils and fats can further improve the stability, effectiveness, and feel during use of ascorbic acid in an aqueous solvent.

Other components commonly used in topical preparations in the fields of pharmaceuticals, quasi-drugs or cosmetics can be included if required within quantitative and qualitative ranges that do not impair quality such as a stable appearance and viscosity and that do not impair the effects of the present invention. Examples include amino acids, irritation reducers, thickeners, preservatives, UV protectants, colorants, dispersants, additional pH regulators, and fragrances. Any of these components can be used alone or in combinations of two or more.

A topical composition of the present invention comprises (A) from 1 to 40% by mass of at least one type selected from the group consisting of ascorbic acid and salts of ascorbic acid, (B) at least 20% by mass of a diol having three carbon atoms, (C) at least one type selected from the group consisting of tocopherol, salts of tocopherol, and derivatives of tocopherol, and (D) water. The mass ratio of component (D) to component (A) is from 0.5 to 5.0 and the topical composition includes less than 20% by mass of glycol ether. If necessary, any of the components mentioned above can be mixed into the topical composition. If necessary, other solvents and commonly used bases for topical compositions can be included to prepare a topical composition in the desired form, which can be a paste, mousse, gel, liquid, emulsion, cream, sheet (supported by a base material), aerosol, or spray. These can be prepared using any method common in the art.

A topical composition of the present invention is preferably a transparent or semi-transparent composition in which the ascorbic acid and/or salts thereof have been solubilized. Here, "solubilization" is defined as follows. The transmittance at the 700 nm wavelength using the ultraviolet-visible absorbance measurement method with, for example, a spectrophotometer or a UV-2450 photoelectric photometer (from Shimadzu Corporation) is in the range from 80 to 100%, preferably from 85 to 100%, and more preferably from 90 to 100%. Here, the transmittance in water is 100%. A solubilized composition of the present invention has a transparent or semi-transparent appearance. More specifically, the transmittance measurement method conforms to the method described in [B] General testing methods, 2. Physical testing methods: spectroscopic measurement methods, 2.24 Ultraviolet visible absorbance measurement methods in the 16th edition of the Japanese Pharmacopoeia.

[Viscosity]

A topical composition of the present invention can be prepared as a composition with the proper and desired viscosity for a topical composition used on the skin. There are no particular restrictions on the viscosity of topical compositions of the present invention. However, the viscosity measured at 25° C. using, for example, an E-type viscometer is usually from 1 to 300 mPa·s, preferably from 1 to 200 mPa·s, more preferably from 1 to 100 mPa·s, and even more preferably from 1 to 50 mPa·s. More specifically, the viscosity measurement method conforms to the method described in [B] General testing methods, 2. Physical testing methods: other measurement methods, 2.53 Viscosity measurement methods, 2. Second rotational viscometer method, 2.1.3 Conical-plate rotation viscometer (cone plate viscometer) in the 16th edition of the Japanese Pharmacopoeia.

[pH]

A topical composition of the present invention should be a liquid with a pH from 1 to 8, but from the standpoint of the stability of ascorbic acid, less irritation of skin and mucous membranes, and good product feel when used on the skin, the pH is preferably from 2 to 7, more preferably from 2 to 6, even more preferably from 2 to 5.0, and still more preferably from 2 to 4.5. It is preferably in the acidic range.

[Applications]

A topical composition of the present invention is particularly effective as a whitening agent, an anti-inflammatory agent or an anti-aging agent, and has, for example, acne treating and preventing effects and antioxidant effects. When applied to the skin, skin clarity is enhanced, moisture is retained, skin texture is smooth, and a roughness suppressing effect may be exhibited. It may also have effects such as making pores inconspicuous, moisturizing the skin, and preventing and treating blemishes.

A topical composition of the present invention can be any type of topical composition in the fields of pharmaceuticals, quasi-drugs, and cosmetics. Examples include basic cosmetics such as liquid foundations, toners, sunscreens, emulsions, creams, lotions, oils and facial masks; makeup such as rouges, lipsticks, lip balms, mascaras, eyeshadow, eyeliners, eyebrow pencils, and nail polish; cleaning agents such as makeup removers, cleansers, and body washes; and deodorants, athlete's foot medications, antipruritic agents, wound healing agents, cleaners, anti-inflammatory analgesics, acne medications, hemorrhoid medications, antiseptic agents, whitening agents, and UV protection agents. From the standpoint of the effect on the skin, the present invention is preferably used as a product applied to the outer skin such as topical preparations for the skin (skin preparations). A composition of the present invention can be used one or more times daily in a commonly used amount and method of administration depending on the intended use.

[Stabilization Method]

The present invention also encompasses a method for stabilizing (A) at least one type selected from the group consisting of ascorbic acid and salts of ascorbic acid. The present invention is a method for obtaining a stable ascorbic acid-containing preparation comprising (A) at least one type selected from the group consisting of ascorbic acid and salts of ascorbic acid by compounding (A) from 1 to 40% by mass of at least one type selected from the group consisting of ascorbic acid and salts of ascorbic acid, (B) at least 20% by mass of a diol having three carbon atoms; (C) at least one type selected from the group consisting of tocopherol, salts of tocopherol, and derivatives of tocopherol, and (D) water, and by setting the mass ratio of component (D) to component (A) mass ratio from 0.5 to 5.0 and the amount of glycol ether at less than 20% by mass. In particular, a stable preparation can be obtained that contains a high concentration of ascorbic acid (for example, 15% or more, or 20% or more). In other words, the present invention relates to a method for imparting stability to a topical composition comprising (A) at least one type selected from the group consisting of ascorbic acid and salts of ascorbic acid by compounding (A) from 1 to 40% by mass of at least one type selected from the group consisting of ascorbic acid and salts of ascorbic acid, (B) at least 20% by mass of a diol having three carbon atoms; (C) at least one type selected from the group consisting of tocopherol, salts of tocopherol, and derivatives of tocopherol, and (D) water, and by setting the mass ratio of component (D) to component (A) mass ratio from 0.5 to 5.0 and the amount of glycol ether at less than 20% by mass. There are no particular restrictions on the nature of the stabilization but can mean, for example, that stability is ensured at high and low temperatures. Specifically, it means the decrease in the ascorbic acid concentration is suppressed when stored at 50° C. or 40° C. and when stored at room temperature.

In the method of the present invention, the topical composition described above is used, which comprises (A) from 1 to 40% by mass of at least one type selected from the group consisting of ascorbic acid and salts of ascorbic acid, (B) at least 20% by mass of a diol having three carbon atoms, (C) at least one type selected from the group consisting of tocopherol, salts of tocopherol, and derivatives of tocopherol, and (D) water, and in which the mass ratio of component (D) to component (A) is from 0.5 to 5.0 and the topical composition includes less than 20% by mass of glycol ether.

The present invention encompasses the following aspects.

[1] A topical composition comprising:
 (A) from 1 to 40% by mass of at least one type selected from the group consisting of ascorbic acid and salts of ascorbic acid;
 (B) at least 20% by mass of a diol having three carbon atoms;
 (C) at least one type selected from the group consisting of tocopherol, salts of tocopherol, and derivatives of tocopherol; and
 (D) water,
 wherein the mass ratio of component (D) to component (A) mass ratio is from 0.5 to 5.0 and the topical composition includes less than 20% by mass of glycol ether.

[2] A topical composition according to [1], further comprising a lower alcohol.

[3] A topical composition according to [2], wherein the lower alcohol is ethanol.

[4] A topical composition according to any one of [2] to [3], wherein the amount of lower alcohol is from 0.001 to 30% by mass.

[5] A topical composition according to any one of [1] to [4], wherein component (B) includes 1,3-propanediol.

[6] A topical composition according to any one of [1] to [5], comprising at least 40% by mass of component (B).

[7] A topical composition according to any one of [1] to [6], comprising no more than 0.5% by mass of component (C).

[8] A topical composition according to any one of [1] to [7], wherein the amount of ethoxydiglycol ether is less than 10% by weight.

The present invention also provides the following method for imparting stability to a topical composition.

[9] A method for imparting stability to a topical composition comprising (A) at least one type selected from the group consisting of ascorbic acid and salts of ascorbic acid by including
 (A) from 1 to 40% by mass of at least one type selected from the group consisting of ascorbic acid and salts of ascorbic acid, (B) at least 20% by mass of a diol having three carbon atoms;
 (C) at least one type selected from the group consisting of tocopherol, salts of tocopherol, and derivatives of tocopherol, and (D) water, and by setting the mass ratio of component
 (D) to component (A) mass ratio from 0.5 to 5.0 and the amount of glycol ether at less than 20% by mass.

[10] The method according to [9], wherein the topical composition further comprises a lower alcohol.

[11] The method according to [10], wherein the lower alcohol is ethanol.

[12] The method according to [10] or [11], wherein the amount of lower alcohol is from 0.001 to 30% by mass.

[13] The method according to any one of [9] to [12], wherein component (B) in the topical composition includes 1,3-propanediol.

[14] The method according to any one of [9] to [13], wherein the topical composition comprises at least 40% by mass of component (B).

[15] The method according to any one of [9] to [14], wherein the topical composition comprises no more than 0.5% by mass of component (C).

[16] A topical composition according to any one of [1] to [7], wherein the amount of ethoxydiglycol ether in the topical composition is less than 10% by weight.

EXAMPLES

The present invention will now be described in detail using examples. The present invention is not limited to the examples below. Note that the unit of the amounts for the components in the table is percent by mass.

The topical compositions with the compositions shown in Tables 1 to 3 were prepared in the usual manner. Except where otherwise indicated, all numerical values in the tables represent mass percentages.

[Ascorbic Acid Stability Test]

Glass containers able to contain 20 g were filled with 15 g of each of the examples and comparative examples and then each glass container was allowed to stand in a constant temperature and humidity chamber. After a period of two or four weeks, the containers were removed from the constant temperature and humidity chambers and, after reaching a constant temperature of 25° C., the change in the amount of ascorbic acid in each container was evaluated.

The ascorbic acid was detected by HPLC with an ultraviolet absorptiometer at a wavelength of 270 nm using a reverse phase column (Inertsil ODS-3 from GL Sciences), and the amount was calculated.

The results of the ascorbic acid stability tests performed on the compositions in the examples and the comparative examples are shown in Tables 1 to 3. For each formulation, the change in the amount of ascorbic acid was indicated by a "rate of improvement" obtained by comparing the same formulations with and without tocopherol to each other. The rate of improvement is calculated using the following equations. Each formulation, with and without tocopherol, were compared and the change in the amount of ascorbic acid is expressed by the "rate of improvement." Note that the amount (mass %) of ascorbic acid after testing is the "residual rate." The rate of improvement is calculated as follows.

Rate of Decrease 1=(100−residual rate of ascorbic acid in tocopherol-free composition)

Rate of Decrease 2=(100−residual rate of ascorbic acid in tocopherol-containing composition)

Rate of Improvement={(Rate of Decrease 1−Rate of Decrease 2)/Rate of Decrease 1}×100(%)

Different compositions with and without tocopherol were used to calculate Rate of Decrease 1 and Rate of Decrease 2. The tocopherol-free compositions were supplemented with the largest amount of polyhydric alcohol.

TABLE 1

Ascorbic Acid Stability (40° C. 4 W) (mass %)

| | Ex. 1 | Ex. 2 | Ex. 3 | Ex. 4 |
|---|---|---|---|---|
| Ascorbic Acid | 7 | 7 | 25 | 7 |
| 1,3-Propanediol (PD) | 35.5 | 55.9 | 32.5 | — |
| Propylene Glycol (PG) | 20 | — | — | 35.5 |
| Purified Water | 25 | 25 | 25 | 25 |
| d-δ-Tocopherol | 0.5 | 0.1 | 0.5 | 0.5 |
| Absolute Ethanol | 10 | 10 | 10 | 10 |
| Polyoxyethylene/Polyoxypropylene Decyltetradecyl Ether | 2 | 2 | 2 | 2 |
| 1,3-Butylene Glycol | — | — | — | 20.0 |
| Ethoxydiglycol | — | — | — | — |
| Dipropylene Glycol | — | — | — | — |
| Trimethylglycine | — | — | 5 | — |
| Total | 100 | 100 | 100 | 100 |
| Rate of Improvement in Ascorbic Acid Concentration (%) | 34.07 | 76.76 | 38.72 | 30 |

| | Ex. 5 | C. Ex. 1 | C. Ex. 2 | C. Ex. 3 |
|---|---|---|---|---|
| Ascorbic Acid | 7 | 7 | 7 | 7 |
| 1,3-Propanediol (PD) | — | — | — | 40.5 |
| Propylene Glycol (PG) | 55.5 | — | — | — |
| Purified Water | 25 | 25 | 25 | 40 |
| d-δ-Tocopherol | 0.5 | 0.5 | 0.5 | 0.5 |
| Absolute Ethanol | 10 | 10 | 10 | 10 |
| Polyoxyethylene/Polyoxypropylene Decyltetradecyl Ether | 2 | 2 | 2 | 2 |
| 1,3-Butylene Glycol | — | — | — | — |
| Ethoxydiglycol | — | — | 55.5 | — |
| Dipropylene Glycol | — | 55.5 | — | — |
| Trimethylglycine | — | — | — | — |
| Total | 100 | 100 | 100 | 100 |
| Rate of Improvement in Ascorbic Acid Concentration (%) | 12.88 | −21.65 | −0.76 | 0 |

It is clear from Table 1 that in formulations containing 1,3-propanediol (PD), the decomposition of ascorbic acid (VC) was lessened by the addition of tocopherol (VE) (Examples 2 and 3). Note that the improvement was unrelated to the VC concentration and VE concentration. A similar improvement can be seen in formulations containing 35.5% by weight or more PG (Examples 4 and 5). A similar tendency was even observed in Example 1, which contains PD and PG.

TABLE 2

Ascorbic Acid Stability (50° C. 4 W) (mass %)

| | Ex. 6 | Ex. 7 | C. Ex. 4 |
|---|---|---|---|
| Ascorbic Acid | 7 | 25.0 | 7 |
| 1,3-Propanediol (PD) | 55.9 | 32.5 | — |
| Propylene Glycol (PG) | — | — | — |
| Purified Water | 25 | 25 | 25 |
| d-δ-Tocopherol | 0.1 | 0.5 | 0.5 |
| Absolute Ethanol | 10 | 10 | 10 |
| Polyoxyethylene/Polyoxypropylene Decyltetradecyl Ether | 2 | 2 | 2 |
| 1,3-Butylene Glycol | — | — | — |
| Ethoxydiglycol | — | — | — |
| Dipropylene Glycol | — | — | 55.5 |
| Trimethylglycine | — | 5 | — |
| Total | 100 | 100 | 100 |
| Rate of Improvement in Ascorbic Acid Concentration (%) | 29.84 | 14.57 | −28.88 |

| | C. Ex. 5 | C. Ex. 6 | C. Ex. 7 |
|---|---|---|---|
| Ascorbic Acid | 7 | 7 | 7 |
| 1,3-Propanediol (PD) | — | — | 40.5 |
| Propylene Glycol (PG) | — | 10.0 | — |
| Purified Water | 25 | 25 | 40 |
| d-δ-Tocopherol | 0.5 | 0.5 | 0.5 |
| Absolute Ethanol | 10 | 10 | 10 |
| Polyoxyethylene/Polyoxypropylene Decyltetradecyl Ether | 2 | 2 | 2 |
| 1,3-Butylene Glycol | — | 30 | — |
| Ethoxydiglycol | 55.5 | — | — |
| Dipropylene Glycol | — | 15.5 | — |
| Trimethylglycine | — | — | — |
| Total | 100 | 100 | 100 |
| Rate of Improvement in Ascorbic Acid Concentration (%) | −1.67 | −11.69 | −2.15 |

It is clear from Table 2 that in formulations containing a high concentration of PD (Examples 6 and 7), the decomposition of ascorbic acid was lessened by the addition of d-δ-tocopherol. However, in prescriptions containing low concentrations of a polyhydric alcohol other than PD or PG and prescriptions containing a large amount of water, the rate of improvement was mild or the addition of d-δ-tocopherol promoted the decomposition of ascorbic acid (Comparative Examples 4 to 7).

TABLE 3

| | Ascorbic Acid Stability (50° C. 2 W) (mass %) | | |
|---|---|---|---|
| | C. Ex. 8 | Ex. 8 | Ex. 9 |
| Ascorbic Acid | 7 | 7 | 7 |
| 1,3-Propanediol (PD) | — | 55.5 | — |
| Propylene Glycol (PG) | — | — | 55.5 |
| Purified Water | 25 | 25 | 25 |
| d-δ-Tocopherol | 0.5 | 0.5 | 0.5 |
| Absolute Ethanol | 10 | 10 | 10 |
| Polyoxyethylene/Polyoxypropylene Decyltetradecyl Ether | 2 | 2 | 2 |
| Dipropylene Glycol | 55.5 | — | — |
| Total | 100 | 100 | 100 |
| Rate of Improvement in Ascorbic Acid Concentration (%) | / | 14.07 | 15.99 |

In Table 3, the ascorbic acid rate of improvement (%) is [{(100−residual rate of ascorbic acid in the composition of Comparative Example 8)−(100−residual rate of ascorbic acid in the composition of each example)}/(100−residual rate of ascorbic acid in the composition of Comparative Example 8)]×100. As shown in Table 3, the formulations containing PD and PG had an improved VC rate relative to the DPG formulation (Examples 8 and 9).

Examples of Formulations

Examples of formulations are shown in Table 4 below. The examples of formulations are all liquid foundations, and the unit amount in each example of a formulation is percent by mass.

TABLE 4

| Component Name | Formulation 1 Amt. (%) | Formulation 3 Amt. (%) | Formulation 3 Amt. (%) | Formulation 4 Amt. (%) |
|---|---|---|---|---|
| Ascorbic Acid | 25 | 20 | 10 | 5 |
| Propylene Glycol | 20.69 | — | 20.89 | 54.2 |
| 1,3-Propanediol | 35 | 55.78 | 35 | 10 |
| Polyethylene Glycol 400 | 2 | 12 | — | 15 |
| 1,3-Butylene Glycol | — | 5 | 10 | 2 |
| Dipropylene Glycol | 10 | — | — | 4 |
| Conc. Glycerin | — | — | 4 | — |
| Abs. Ethanol | 5 | 5 | 8 | 8 |
| Fragrance | 0.3 | 0.3 | 0.3 | 0.3 |
| Polyoxyethylene Hardened Sesame Oil 40 | — | — | — | — |
| Jojoba Oil | — | — | — | — |
| Polyoxyethylene (20) Polyoxyethylene (4) Cetyl Ether | — | — | 0.2 | 0.2 |
| Polyoxyethylene Polyoxypropylene Decyltetradecyl Ether | 0.2 | 0.2 | — | — |
| Trimethyl Glycine | 0.5 | 0.5 | — | — |
| L-Carnitine | — | — | 0.3 | — |
| d-δ-Tocopherol | 0.1 | 0.01 | — | — |
| d 1-δ-Tocopherol | — | — | 0.1 | — |
| d 1-α-Tocopheryl Acetate | — | — | — | 0.1 |
| Grapefruit Extract | 0.5 | 0.5 | 0.5 | 0.5 |
| Lemon Extract | 0.5 | 0.5 | 0.5 | 0.5 |
| Kiwi Extract | 0.1 | 0.1 | 0.1 | 0.1 |
| Artichoke Extract | 0.1 | 0.1 | 0.1 | 0.1 |
| Ethoxydiglycol | — | — | 10 | — |
| Na Hyaluronate | 0.01 | 0.01 | 0.01 | — |
| Purified Water | 20 | 16 | 12 | 10 |
| Total | 100 | 100 | 100 | 100 |

| Component Name | Formulation 5 Amt. (%) | Formulation 6 Amt. (%) | Formulation 7 Amt. (%) | Formulation 8 Amt. (%) |
|---|---|---|---|---|
| Ascorbic Acid | 5 | 3 | 3 | 1 |
| Propylene Glycol | 28.59 | 39.49 | 30.5 | 22.589 |
| 1,3-Propanediol | 30 | 35 | 50 | 60 |
| Polyethylene Glycol 400 | 15 | 10 | — | — |
| 1,3-Butylene Glycol | 10 | 0.1 | 5 | 5 |
| Dipropylene Glycol | — | 10 | — | — |
| Conc. Glycerin | — | — | — | — |
| Abs. Ethanol | 10 | — | 10 | 10 |
| Fragrance | 0.3 | 0.3 | — | — |
| Polyoxyethylene Hardened Sesame Oil 40 | — | 0.2 | — | — |
| Jojoba Oil | 0.1 | — | — | — |
| Polyoxyethylene (20) Polyoxyethylene (4) Cetyl Ether | 0.4 | 0.2 | — | — |
| Polyoxyethylene Polyoxypropylene Decyltetradecyl Ether | — | — | 0.2 | 0.2 |
| Trimethyl Glycine | 0.1 | — | — | — |
| L-Carnitine | — | — | — | — |
| d-δ-Tocopherol | 0.1 | 0.5 | 0.1 | 0.001 |
| d 1-δ-Tocopherol | — | — | — | — |
| d 1-α-Tocopheryl Acetate | — | — | — | — |
| Grapefruit Extract | 0.1 | 0.5 | 0.5 | 0.5 |
| Lemon Extract | 0.1 | 0.5 | 0.5 | 0.5 |
| Kiwi Extract | 0.1 | 0.1 | 0.1 | 0.1 |
| Artichoke Extract | 0.1 | 0.1 | 0.1 | 0.1 |
| Ethoxydiglycol | — | — | — | — |
| Na Hyaluronate | 0.01 | 0.01 | — | 0.01 |
| Purified Water | 4 | 6 | 2 | 2 |
| Total | 100 | 100 | 100 | 100 |

The invention claimed is:

1. A topical composition comprising:
   (A) from 1 to 10% by mass of at least one type selected from the group consisting of ascorbic acid and salts of ascorbic acid;
   (B) at least 40% by mass of 1,3-propanediol;
   (C) at least one type selected from the group consisting of tocopherol, salts of tocopherol, and derivatives of tocopherol; and
   (D) water;
   wherein the mass ratio of component (D) to component (A) is from 0.5 to 5.0 and the topical composition includes less than 20% by mass of glycol ether.

2. A topical composition according to claim 1, comprising no more than 0.5% by mass of component (C).

3. A topical composition according to claim 1, wherein the topical composition includes less than 10% by mass of ethoxydiglycol ether.

4. A method for imparting stability to the topical composition of claim 1, comprising steps of:
   compounding (A) from 1 to 10% by mass of at least one type selected from the group consisting of ascorbic acid and salts of ascorbic acid, (B) at least 40% by mass of 1,3-propanediol, (C) at least one type selected from the group consisting of tocopherol, salts of tocopherol, and derivatives of tocopherol, and (D) water, and
   setting the mass ratio of component (D) to component (A) from 0.5 to 5.0 and the amount of glycol ether at less than 20% by mass.

* * * * *

UNITED STATES PATENT AND TRADEMARK OFFICE
CERTIFICATE OF CORRECTION

PATENT NO. : 12,296,038 B2
APPLICATION NO. : 17/279296
DATED : May 13, 2025
INVENTOR(S) : Yu Kitaoka, Mariko Iwai and Sho Yamashina It is certified that error appears in the above-identified patent and that said Letters Patent is hereby corrected as shown below:

In the Specification

Column 4; Line 16: "[(C) at" should read --[(C) At--

Column 7; Line 4: "acid, s-aminocaproic acid," should read --acid, ε-aminocaproic acid,--

Signed and Sealed this
First Day of July, 2025

Coke Morgan Stewart
*Acting Director of the United States Patent and Trademark Office*